US006726479B2

(12) United States Patent
Tremont

(10) Patent No.: US 6,726,479 B2
(45) Date of Patent: Apr. 27, 2004

(54) METHOD AND APPARATUS TO ASSIST IN ORTHOGNATHIC SURGERY

(76) Inventor: Timothy J. Tremont, 3 Concord Dr., McKeesport, PA (US) 15135

( * ) Notice: Subject to any disclaimer, the term of this patent is extended or adjusted under 35 U.S.C. 154(b) by 25 days.

(21) Appl. No.: 10/054,518

(22) Filed: Jan. 22, 2002

(65) Prior Publication Data

US 2003/0138755 A1 Jul. 24, 2003

(51) Int. Cl.[7] ............................................. A61C 19/04

(52) U.S. Cl. ............................. 433/72; 433/68; 33/513

(58) Field of Search .......................... 433/68, 69, 72, 433/73, 75; 33/513, 514

(56) References Cited

U.S. PATENT DOCUMENTS

| 4,189,835 A | | 2/1980 | Seldin ........................ 433/214 |
| 4,573,917 A | | 3/1986 | Erickson ...................... 433/75 |
| 4,639,220 A | * | 1/1987 | Nara et al. .................... 433/69 |

OTHER PUBLICATIONS

G. Alastair Wylie et al.,"A Technique to Improve the Accuracy of Total Maxillary Surgery" from The International Journal of Adult Orthodontics and Orthognathic Surgery Mar. 1988, pp. 143–147.
Kim L. Erickson et al., "Analytical Model Surgery" from Modern Practice in Orthognathic and Reconstructive Surgery vol. 1, pp. 155, 177, 178, and 179, 1992.
Nadejda Stefanova et al., "The Predictability of Inferior Medial Canthus as a Stable External Vertical Reference Point in Maxillary Repositioning Surgery" from International Journal of Adult Orthodontics and Orthognathic Surgery, vol. 15, No. 4, 2000, pp. 305–308.
Ltc. Steven J. Perkins et al., "A Modified Boley Gauge for Accurate Measurement During Maxillary Osteotomies" from Journal of Oral Maxillofacial Surgery, 50:1018–1019, 1992, pp. 1018–1019.
Undated letter from Steven J. Perkins D.D.S. with attached brochure entitled Surgical Instruments Perkins Maxillary Measuring Gauge.
William H. Bell et al., "Art of Science of the Le Fort I Downfracture" in The International Journal of Adult Orthodontics and Orthognathic Surgery, vol. 3, No. 1, 1988, pp. 23–52.

(List continued on next page.)

*Primary Examiner*—John J. Wilson
(74) *Attorney, Agent, or Firm*—Paul A. Beck & Assoc.

(57) ABSTRACT

A method and apparatus to assist in accurate placement of teeth and jaws at orthognathic surgery. A recording of reference planes used prior to surgery to plan desired changes to an original position of teeth and jaws of a patient is made with a teeth indexing member. The teeth indexing member has a horizontal slot and scribe lines indicating the orientation of the reference planes. During surgery, the recording of the reference planes is transferred to the patient by positioning the teeth indexing member onto the patient's teeth. A swivel member is attached to the patient's head by a cranial structure. A port in the swivel member is oriented to the reference planes by inserting a coupling member into the horizontal slot of the teeth indexing member and into the port of the swivel member, aligning the coupling member to the scribe lines on the teeth indexing member, and securing the oriented swivel member in place. The port thereby records the reference planes. With the teeth indexing member removed and the coupling member reinserted into the oriented port of the swivel member, the coupling member can measure an original position of the teeth and jaws and indicate desired changes to the original position of the teeth and jaws relative to the reference planes in x-, y-, and z-dimensions. An indicator member when independently inserted into the slot of the teeth indexing member assists in designing osteotomies relative to the reference planes.

22 Claims, 13 Drawing Sheets

OTHER PUBLICATIONS

Rainer Schwestka–Polly, "Significance of the Contour of the Lateral Surface of the Maxilla for Planning Osteotomy Lines in Orthognathic Surgery" in The International Journal of Adult Orthodontics and Orthognathic Surgery, vol. 8, No. 3, 1993, pp. 191–201.

A.A.C. Heggie, "A Calibrator for Monitoring Maxillary Incisor Position During Orthognathic Surgery" from Oral Surg., vol. 64, No. 6, Dec. 1987, pp. 671–673.

Louis M. Manna et al., "Technique for Vertical Positioning of the Maxilla After Le Fort Osteotomy" from Journal of Oral Maxillofacial Surgery, 54:652, 1996, p. 652.

Joseph E. Van Sickels et al., "Predictability of Maxillary Surgery: A Comparison of Internal and External Reference Marks" from Oral Surg., vol. 61, No. 6, Jun. 1986, pp. 542–545.

Waldemar D. Polido et al., "An Assessment of the Predicability of Maxillary Surgery" from Journal of Oral Maxillofacial Surgery, 48:697–701, 1990, pp. 697–701.

D.G. Johnson et al., "Intraopterative Measurement of Maxillary Repositioning: An Ancillary Technique" from Oral Surg., vol. 60, No. 3, Sep. 1985, pp. 266–268.

Brochure—W. Lorenz "Bluedevice" Multi–Vector Distraction (undated).

Brochure—KLS Martin L.P. "Rigid External Distraction RED II System" (undated).

* cited by examiner

METHOD AND APPARATUS TO ASSIST IN ORTHOGNATHIC SURGERY

BACKGROUND OF THE INVENTION

1. Field of the Invention

The applicant's invention is a method and apparatus for use in orthognathic surgery. This type of surgery involves the correction of dentofacial deformities and is also referred to as maxillofacial surgery, reconstructive jaw surgery or surgical orthodontics.

During orthognathic surgery teeth and jaws of a patient are repositioned. Prior to surgery, desired changes to an original position of the patient's teeth and jaws can be determined by clinical evaluation of the patient's head, evaluation of the patient's head X-ray, and evaluation of articulator mounted dental models. The desired changes to the teeth and jaws can be measured in three dimensions, parallel and perpendicular to reference planes. Three reference planes that can be used are a horizontal plane, a sagittal plane and a frontal plane. The horizontal plane is defined by three points on the patient's head. The sagittal and frontal planes are perpendicular to each other as well as to the horizontal plane. The reference planes are common to the patient's head, head X-ray and articulator mounted dental models. The desired changes to the teeth and jaws can be described in terms of x-, y-, and z-dimensions. The surgeon attempts to make actual changes to the original position of the teeth and jaws that are identical to the desired changes.

2. Description of Related Art

Prior art has been published by G. Wylie, B. Epker and J. Mosop in the *International Journal of Adult Orthodontics and Orthognathic Surgery*, 1988; 3:143–147. A technique is described to assist in designing osteotomies using a maxillary measuring appliance. The device consists of a horizontal table indexed to the teeth and having an adjustable calibrated vertical pillar that can slide along the length of the horizontal table. This technique is deficient in that orientation of the horizontal table is limited to a row of teeth as a reference line. Also, it is limited to one side of a dental arch at a time. Measuring as well as marking osteotomy lines is inaccurate due to parallax problems. Osteotomies cannot be designed in a continuous manner on both sides of a jaw. In addition, the device is limited to designing osteotomies and cannot measure and record an original position of or actual changes to teeth and jaws relative to reference planes.

A prior art method of measuring the actual changes to the teeth and jaws during surgery has been described by Erikson in Chapter 7 of the text titled *Modern Practice in Orthognathic and Reconstructive Surgery*, 1992, W. B. Saunders Company. He presents a technique whereby the surgeon uses calipers to obtain a vertical measurement prior to a maxillary osteotomy from a point on a cuspid tooth to a scribed mark on a maxilla superior to the osteotomy. A second measurement is made between the same two points after the jaw is repositioned in order to assess the actual changes.

Erikson's technique is deficient in obtaining accurate measurements. It is difficult to measure the site with calipers due to parallax error. Measurements are limited to an intended y-dimension and exclude the x- and z-dimensions. The vertical measurement cannot predictably be made perpendicular to the same reference plane used prior to surgery to describe desired changes.

Other prior art was published by Perkins in the *Journal of Oral and Maxillofacial Surgery*, 1992; 50:1018–1019. He described an instrument manufactured and sold by Walter Lorenz Surgical, Inc of Jacksonville, Fla. It consists of a modified Boley gauge whose upper caliper is slipped onto a K-wire inserted into and extending from a skull in a nasofrontal region. A lower caliper has a wire extending from it that is approximated to a point of measurement on the teeth and jaws. Once measured, an original position of the teeth and jaws is changed by surgery and the same point is measured again. A difference in measurements indicates an actual change from the original position. Perkins' method is deficient because it cannot predictably measure perpendicular to presurgical reference planes in x- and y-dimensions. Also, it cannot measure in a z-dimension.

Additional prior art was described by N. Stefanova and J. Stella in *The International Journal of Adult Orthodontics and Orthopedic Surgery*, 2000; 15:305–308. It involves using a large orthopedic caliper to make a measurement of an original position of teeth and jaws from an inferior medial canthus of an eye to a point on a tooth. A second measurement is made between the same points after the teeth and jaws are repositioned. The difference between the two measurements purportedly describes actual changes. This method is deficient in that it is difficult to reposition the caliper exactly the same way for each measurement. It cannot predictably measure relative to a presurgical reference plane in a y-dimension. Also, it cannot measure in x- or z-dimensions.

The applicant's invention is a method and apparatus that assists a surgeon in making actual changes to teeth and jaws that are accurate with desired changes. The invention solves the problems inherent to prior art. It enables a surgeon at surgery to measure perpendicular and parallel to reference planes used prior to surgery to measure desired changes. Measurements can be made and described in x-, y-, and z-dimensions. The invention also enables the surgeon to measure and design osteotomies of a jaw that are accurately related to the presurgical reference planes in three dimensions.

BRIEF SUMMARY OF INVENTION

The applicant's invention is a method and apparatus that assists a surgeon in making actual changes to an original position of a patient's teeth and jaws that are accurate with desired changes that were determined before surgery. The invention solves the problems inherent to prior art.

Using a known method prior to surgery, the patient's dental models are mounted on an articulator, a known device, so that the models accurately reflect an orientation of the teeth and jaws to the patient's jaw joints and to three reference planes of the patient's head. The reference planes can be a horizontal plane, a sagittal plane and a frontal plane.

Also using known methods before surgery, desired changes to the teeth and jaws can be determined by evaluating the patient's head, head x-ray and articulator mounted dental models. The desired changes to the teeth and jaws are measured relative to the chosen reference planes which are common to the patient's head, head x-ray and articulator mounted dental models.

The invention assists the surgeon in accurate placement of the teeth and jaws by comparing the actual changes to the original position of the teeth and jaws with the desired changes to the teeth and jaws relative to the reference planes. This comparison is done by first recording the reference planes on a teeth indexing member prior to surgery. The recording of the reference planes is then transferred at surgery to the patient's head by placing the teeth indexing member onto the patient's teeth.

A port in a swivel member, which is fastened to the patient's head with a cranial structure, is oriented to the reference planes by coupling it to the teeth indexing member with a coupling member. The swivel member is secured in place and the teeth indexing member is removed. The port in the swivel member now records the reference planes.

Using the coupling member, the oriented port of the swivel member is then coupled to a reference member which is positioned to a defined point on the teeth and jaws. The reference member indicates the original position of the teeth and jaws in any one of the x-, y-, or z-dimensions, or any combination of the x-, y-, and z-dimensions before the original position of the teeth and jaws are changed. The original position of the teeth and jaws in any one of the x-, y-, or z-dimensions, or any combination of the x-, y-, and z-dimensions is measured on the coupling member.

The reference member is adjusted to indicate the desired changes to the original position of the teeth and jaws. Surgery is then preformed which changes the original position of the teeth and jaws. The actual changes to the original position of the teeth and jaws in any one of the x-, y-, or z-dimensions, or combination of the x-, y-, and z-dimensions is compared with the desired changes to the original position of the teeth and jaws in any one of the x-, y-, or z-dimensions, or combination of the x-, y-, and z-dimensions. This is done by comparing the position of the adjusted reference member to the defined point on the teeth and jaws after the original position of the teeth and jaws is changed.

The invention provides a teeth indexing member with a horizontal slot and perpendicular scribe lines on its top surface. The teeth indexing member can be oriented to the articulator mounted dental models so that the horizontal slot parallels the horizontal reference plane and the scribe lines correspond to the sagittal and frontal reference planes. The teeth indexing member is indexed to the teeth of the patient's articulator mounted dental models using an acrylic-like material.

The invention provides a swivel member with a rectangular port that is secured to the patient's head with a cranial structure. The port of the swivel member is oriented to the horizontal slot and to the scribe lines of the teeth indexing member by inserting a rectangular horizontal rod of a coupling member. The port of the swivel member can be secured in place and thereby record the reference planes.

The invention provides a coupling member which consists of a calibrated rectangular horizontal rod which inserts into the rectangular port of the swivel member. A calibrated rectangular vertical rod is slidably supported perpendicular to the horizontal rod. A calibrated reference member is slidably supported perpendicular to the vertical member.

The invention also provides a method to assist in accurate placement of teeth and jaws of a patient during orthognathic surgery by designing desired osteotomies. Reference planes are recorded on a teeth indexing member prior to surgery. The teeth indexing member is positioned onto the patient's teeth at surgery. An indicator member is used to design an osteotomy on a patient's jaw. The osteotomy is compared with the reference plane.

The invention provides an indicator member that consists of a rod, which can be slidably engaged with a horizontal slot of a teeth indexing member, and a pointer that is slidably supported in a right angle manner by the rod. A tip of the pointer is directed in a nonparallel manner away from a perpendicular section of the pointer. Additional teeth indexing members can be oriented and indexed at various angles to the reference planes to permit the surgeon to accurately design and measure osteotomies at various angles to the reference planes.

DETAILED DESCRIPTION OF INVENTION

Definitions

Figure 1:
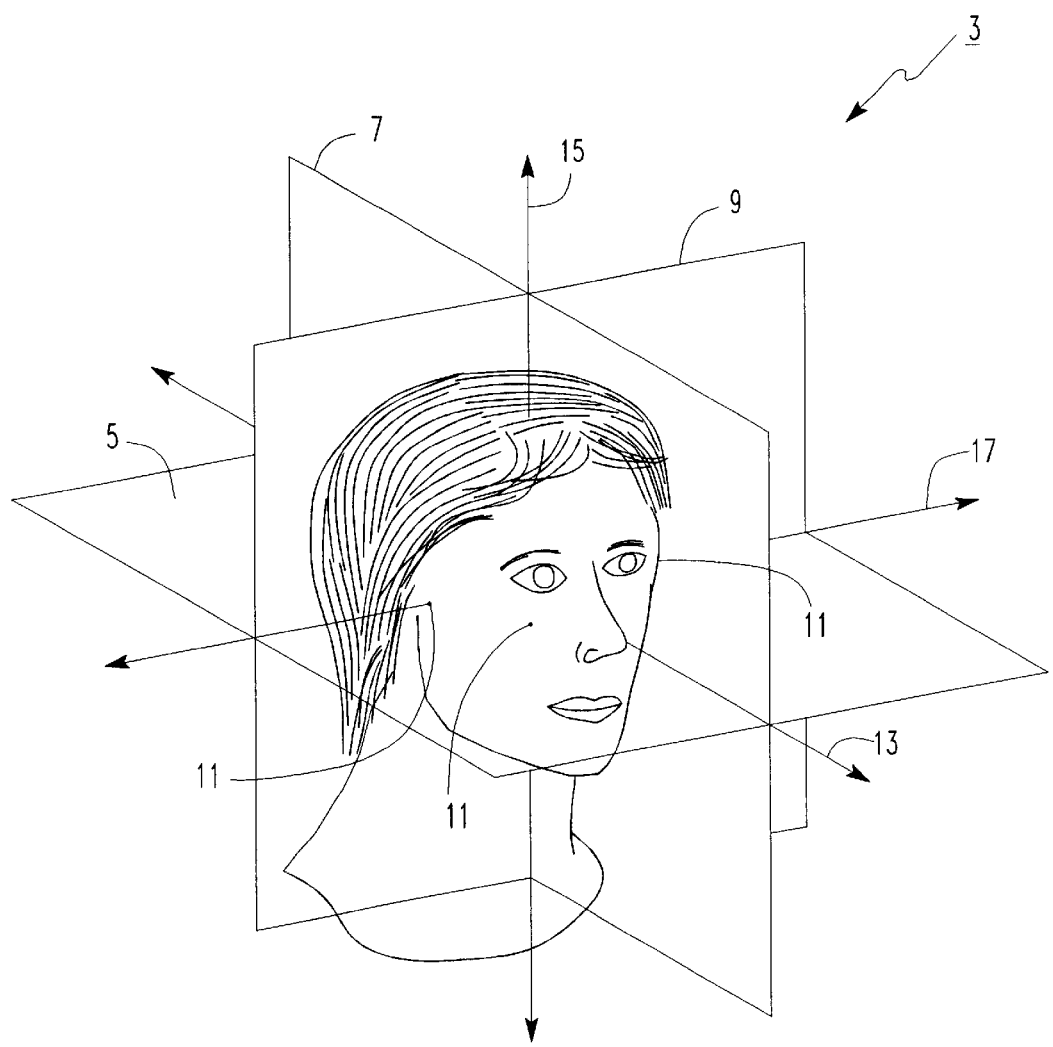
FIG. 1 is an isometric view of a human head with a depiction of horizontal, sagittal and frontal reference planes and lines depicting x-, y-, and z-dimensions.

Accurate placement—actual changes to an original position of a patient's teeth and jaws that are the same as desired changes to the original position of the teeth and jaws.

Acrylic-like material—can be an initially soft plastic material used to index teeth of a dental model. When hardened, it maintains a permanent index of the teeth.

Actual changes—the real change to an original position of teeth and jaws during orthognathic surgery. The change can be measured and described in x-, y-, or z-dimensions relative to reference planes.

Adjusting—moving or repositioning.

Articulator—a known mechanical device that simulates a patient's jaws and jaw joints.

Base member—can be a part of an apparatus that houses a swivel member.

Calibrations—can be marked gradations to indicate measurements.

Coupling bade—can be a part of an indicator member that extends from a handle of the indicator. It has parallel and flat top and bottom surfaces and can be inserted into and slide around a slot of a teeth indexing member.

Coupling member—can be part of an apparatus that links a port of a swivel member to a teeth indexing member. It can consist of a horizontal rod, a vertical rod and a reference member. It can be used to orient the port of the swivel member as well as indicate an original position of teeth and jaws and desired changes to the teeth and jaws.

Cranial structure—can be an apparatus used to secure a swivel member to a patient's head. It consists of a base member and two support structures.

Defined point—an identified spot.

Design an osteotomy—can mean to mark or otherwise indicate a position and shape of an osteotomy.

Desired changes—intended changes to an original position of teeth and jaws determined prior to orthognathic surgery. The changes can be described in x-, y-, and z-dimensions relative to reference planes.

Desired osteotomy—an intended osteotomy that can assist in making a desired change to an original position of a patient's teeth and jaws.

Determine an osteotomy design—can mean to evaluate and decide upon a location, size, and angulation of an osteotomy.

Directed away in a nonparallel manner—oriented so as to point in a diverging direction.

Frontal reference plane—can be a plane oriented in such a manner that it divides a head into front and back sections. It is perpendicular to horizontal and sagittal reference planes.

Handle—can be a part of an indicator member that slidably supports a perpendicular section of a pointer and to which a coupling blade is secured.

Horizontal reference plane—can be a plane defined by three points on a patient's head and representing a transverse plane of the head. It is perpendicular to frontal and sagittal reference planes.

Horizontal rod—can be a part of a coupling member that inserts into a port of a swivel member. It can have calibrations to measure in an x-dimension.

Indicate an osteotomy design—can mean to mark, scribe or otherwise demarcate an osteotomy.

Indicator member—can be an apparatus used to design, measure, or indicate osteotomies relative to a reference plane.

Mounted—attached to. A patient's dental models can be mounted to an articulator using plaster.

Movable ball—can be a spherical swivel member with a port that can be oriented in x-, y-, and z-dimensions relative to reference planes.

Oriented swivel member—a swivel member in which a port in the swivel member is aligned relative to reference planes.

Orienting a swivel member—positioning a swivel member so that a port in the swivel member is aligned relative to reference planes.

Original position of the teeth and jaws—a location of teeth and jaws prior to orthognathic surgery.

Orthognathic surgery—surgery that involves correction of dentofacial deformities. It can mean surgical repositioning of teeth and jaws.

Osteotomy—a surgical cut through bone. It can mean more than one surgical cut.

Parallel—a geometric term meaning a nonconverging relationship of an object or direction to another object or direction.

Perpendicular—a geometric term meaning a converging right angle relationship of an object or direction to another object or direction.

Plate—can be a flat surfaced disk-like object.

Pointer—can be a part of an indicator member that can indicate an osteotomy. It can have a vertical section which is perpendicular to a rod of the indicator member and a tip directed away from the perpendicular section.

Port—an opening; can be rectangular in shape.

Presurgical workup—can be planning of desired changes to an original position of a patient's teeth and jaws including evaluating the patient's head, head X-ray and articulator mounted dental models prior to orthognathic surgery.

Recording—registering something to allow for reproduction; a registration of something.

Reference member—can be part of a coupling member that inserts into a slot of a teeth indexing member in order to orient a port of a swivel member. It can be positioned to a defined point on a patient's teeth and jaws to indicate an original position of and desired changes to the teeth and jaws. It has calibrations to measure in a z-dimension.

Reference plane—a geometric concept; an imaginary flat surface that can be defined by three points or a line and a point. Direction of measurements can be described by their orientation to a reference plane. Other reference planes can be defined in relation to an already defined reference plane. A line drawn on a head x-ray can represent a reference plane.

Relative to the reference plane—compared or measured to a reference plane; described in terms of x-, y-, or z-dimensions defined by a reference plane.

Sagittal reference plane—can be a plane oriented in such a manner that it divides a head into right and left sections. It is perpendicular to horizontal and frontal reference planes.

Securing—attaching or making immovable.

Slidably supported—attached to a structure in a manner that permits movement.

Slot—can be a groove.

Support structure—can be an arm-like part of a cranial structure that secures a base member to a patient's head.

Swivel member—a structure that can turn freely; can be a movable ball housed in a base member of a cranial structure. It can have a port that can be oriented to a reference plane.

Target—can be an identified point, object, or place which indicates a desired position of teeth and jaws.

Teeth and jaws—anatomic parts of a human head which can be repositioned by orthognathic surgery. Teeth and jaws can mean teeth or jaws.

Teeth indexing member—can be a flat surfaced plate with a horizontal slot; can be used to record a reference plane.

Tooth indexable top surface—a surface that can be used to make a registration of teeth.

Toward the coupling blade—can be pointing in the same direction as a coupling blade.

Transfer—relocate.

Vertical rod—can be a part of a coupling member that is slidably supported perpendicular to a horizontal rod. It can have calibrations to measure in a y-dimension.

Vice-like manner—securing by tightening from opposite sides.

x-, y-, and z-dimensions—geometry terms; used to describe directions relative to reference planes when referring to a patient's head. The x-dimension can be in a front-back direction parallel to horizontal and sagittal reference planes and perpendicular to a frontal plane. The y-dimension can be in a vertical direction parallel to the frontal and sagittal reference planes and perpendicular to the horizontal reference plane. The z-dimension can be in a right-left direction parallel to the horizontal and frontal reference planes and perpendicular to the sagittal reference plane.

Description

The applicant's invention is a method and apparatus that assists a surgeon in accurate placement of a patient's teeth and jaws by comparing actual changes to an original position of the teeth and jaws at surgery to desired changes to the original position of the teeth and jaws determined prior to surgery. These changes are measured and compared relative to reference planes in x-, y-, and z-dimensions. The invention can also assist the surgeon in designing and measuring osteotomies relative to the reference planes.

Using a known method prior to surgery, the patient's dental models are mounted on an articulator, a known device, so that the models accurately reflect the orientation of the teeth and jaws to the patient's jaw joints and to three reference planes of the patient's head. As seen in FIG. 1, the reference planes can be a horizontal plane 5, a sagittal plane 7, and a frontal plane 9. The horizontal reference plane 5 is chosen by defining three points 11 on the patient's head before surgery 3. The sagittal 7 and frontal 9 reference planes are perpendicular to each other and to the horizontal reference plane 5.

Figure 2:
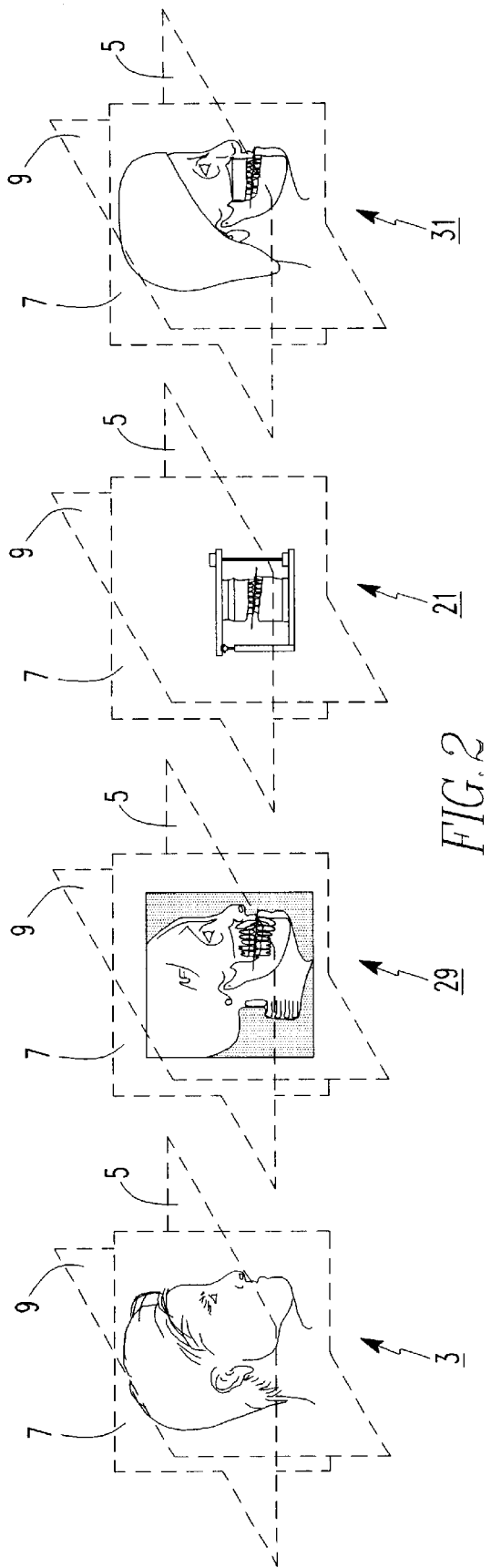
FIG. 2 is a view depicting horizontal, sagittal, and frontal reference planes that are common to a patient's head before surgery, the patient's head X-ray, the patient's articulator mounted dental models, and the patient's head at surgery.

Also using known methods prior to surgery, desired changes to the original position of the teeth and jaws can be determined by evaluating the patient's head, head X-ray and articulator mounted dental models. As seen in FIG. 2, the reference planes are common to the patient's head before surgery 3, head X-ray 29, and articulator mounted dental models 21. Using known methods, the desired changes can be measured in the x-, y-, and z-dimensions 13, 15, 17 relative to the reference planes as seen in FIGS. 1 and 2.

Figure 3:
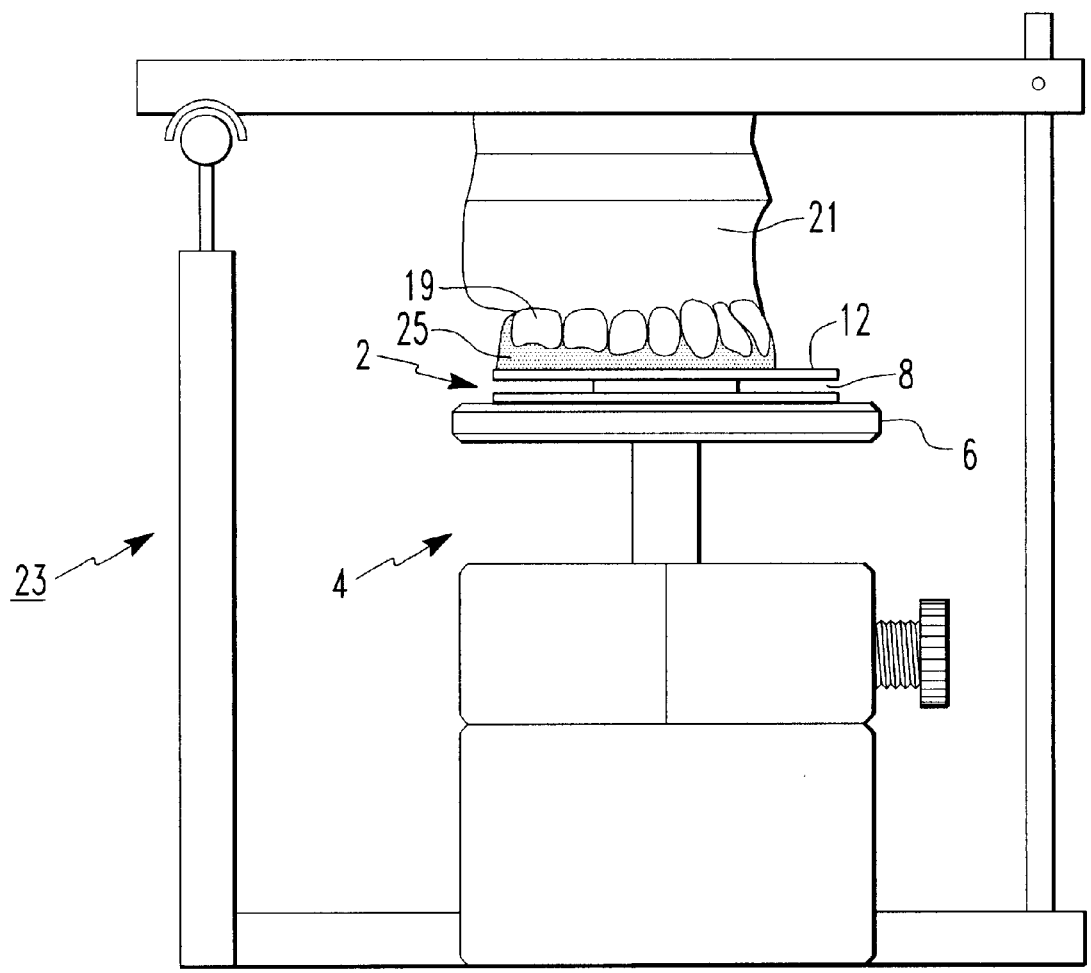
FIG. 3 is a side elevation view depicting the recording of horizontal, sagittal, and frontal reference planes from an articulator mounted dental model with a teeth indexing member.
Figure 4:
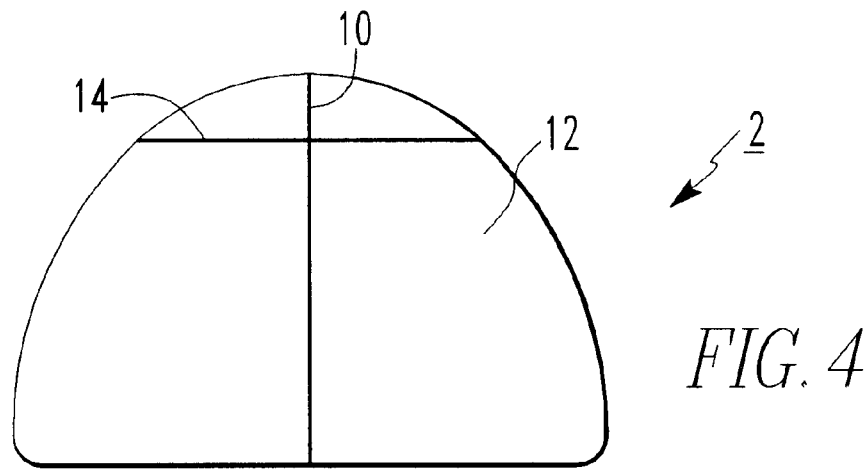
FIG. 4 is a top plan view of a teeth indexing member.
Figure 5:
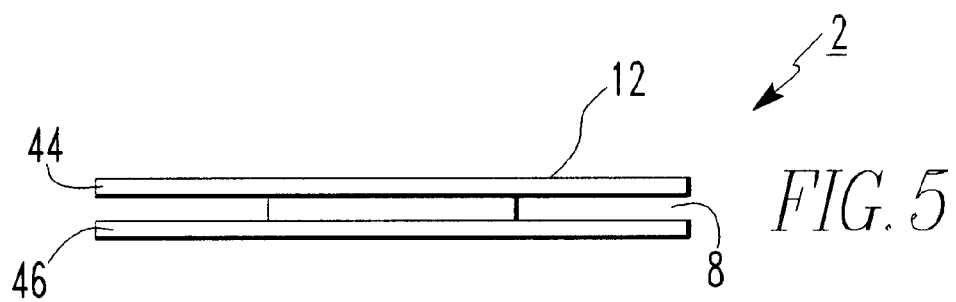
FIG. 5 is an end elevation view of a teeth indexing member.
Figure 6:
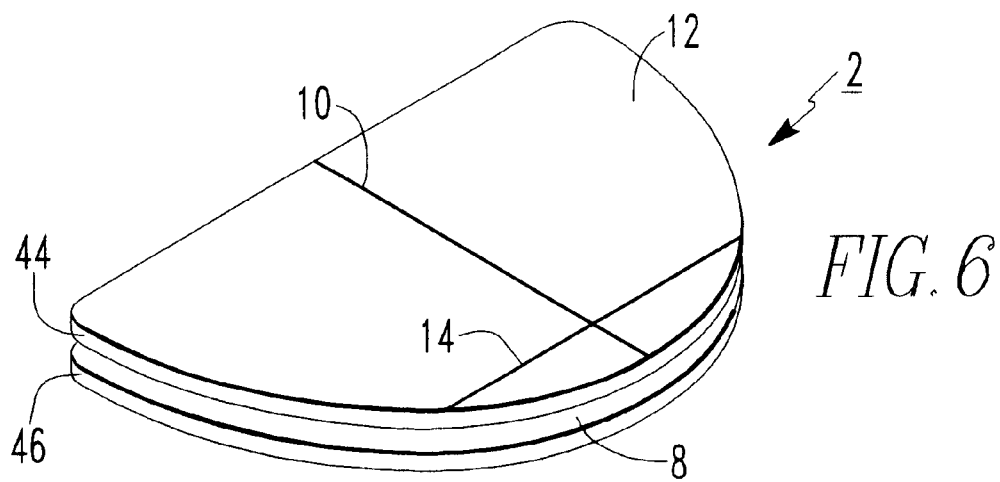
FIG. 6 is an isometric view of a teeth indexing member.
Figure 7:
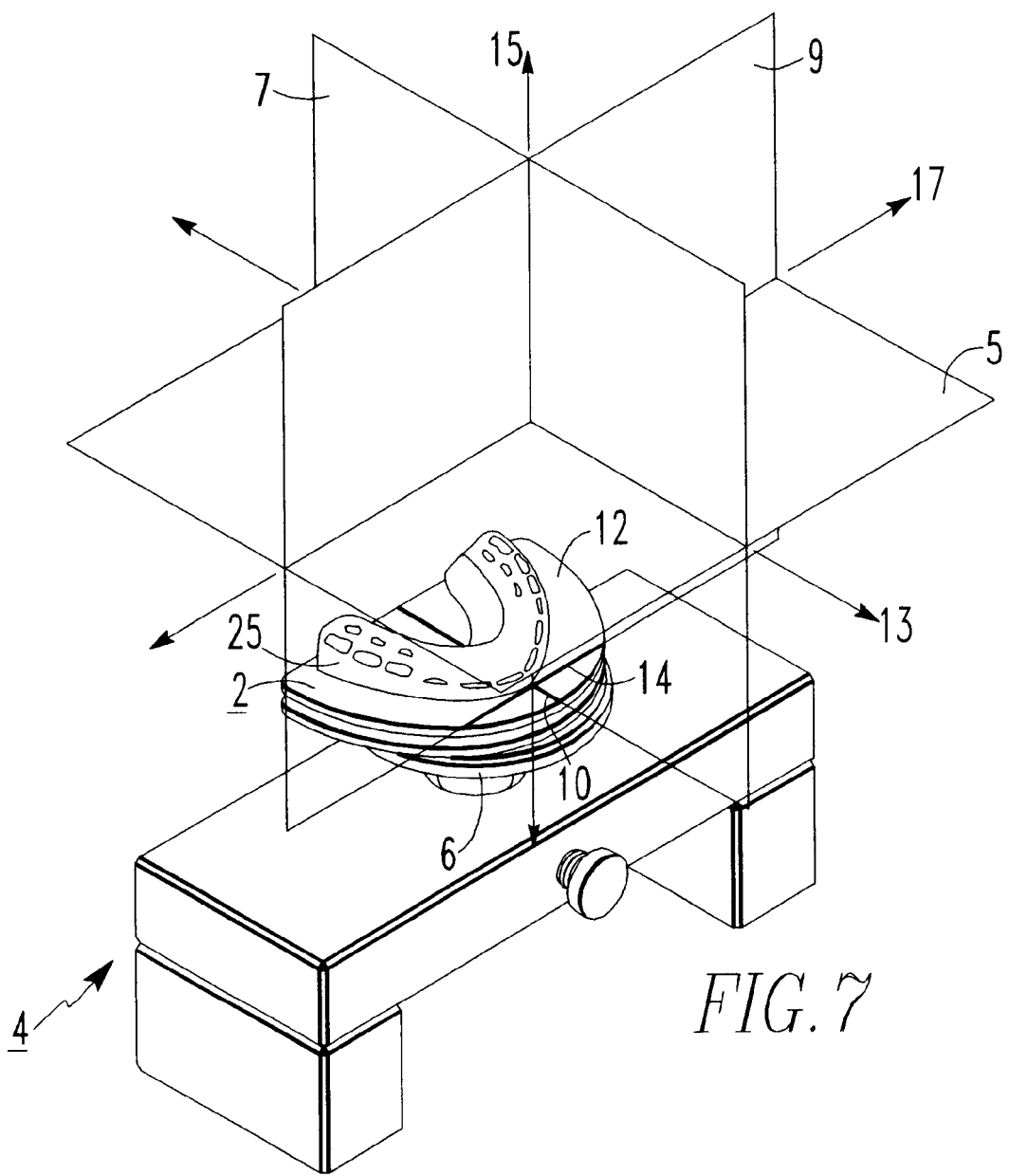
FIG. 7 is an isometric view of a teeth indexing member on an elevator depicting recorded horizontal, sagittal, and frontal reference planes.

As seen in FIG. 3, the invention involves placing a teeth indexing member 2 on an elevator 4 and orienting the teeth indexing member 2 below the teeth 19 of the articulator 23 mounted dental model 21. The elevator 4 straddles the articulator 23. By design, an elevator platform 6 is parallel to the horizontal reference plane 5 of the patient's head 3, head X-ray 29 and articulator mounted dental models 21. A horizontal slot 8 in the teeth indexing member 2 is, therefore, parallel to the horizontal reference plane 5. As seen in FIGS. 4–6, a sagittal scribe line 10 on a top surface 12 of the teeth indexing member 2 is oriented parallel to the sagittal reference plane 7 and a frontal scribe line 14 is concurrently oriented parallel to the frontal reference plane 9. The top surface 12 of the teeth indexing member 2 is then indexed to the teeth 19 of the dental model 21 using an acrylic-like material 25, as seen in FIG. 3. The teeth indexing member 2 now records the reference planes 5, 7, and 9, as seen in FIG. 7. At surgery, the surgeon places the teeth indexing member 2 against the patient's teeth and effectively transfers the recording of the presurgical reference planes to the patient's head at surgery 31 as indicated in FIGS. 2 and 8.

Figure 9:
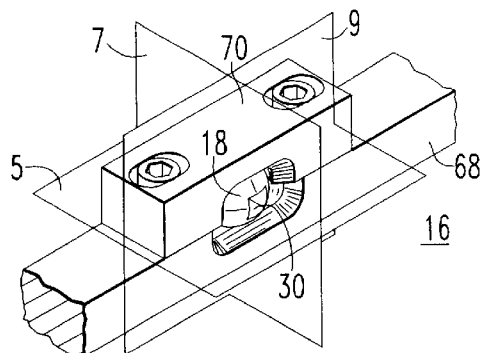
FIG. 9 is an isometric view depicting recorded horizontal, sagittal, and frontal reference planes by a port in a swivel member which is secured in a base member.
Figure 8:
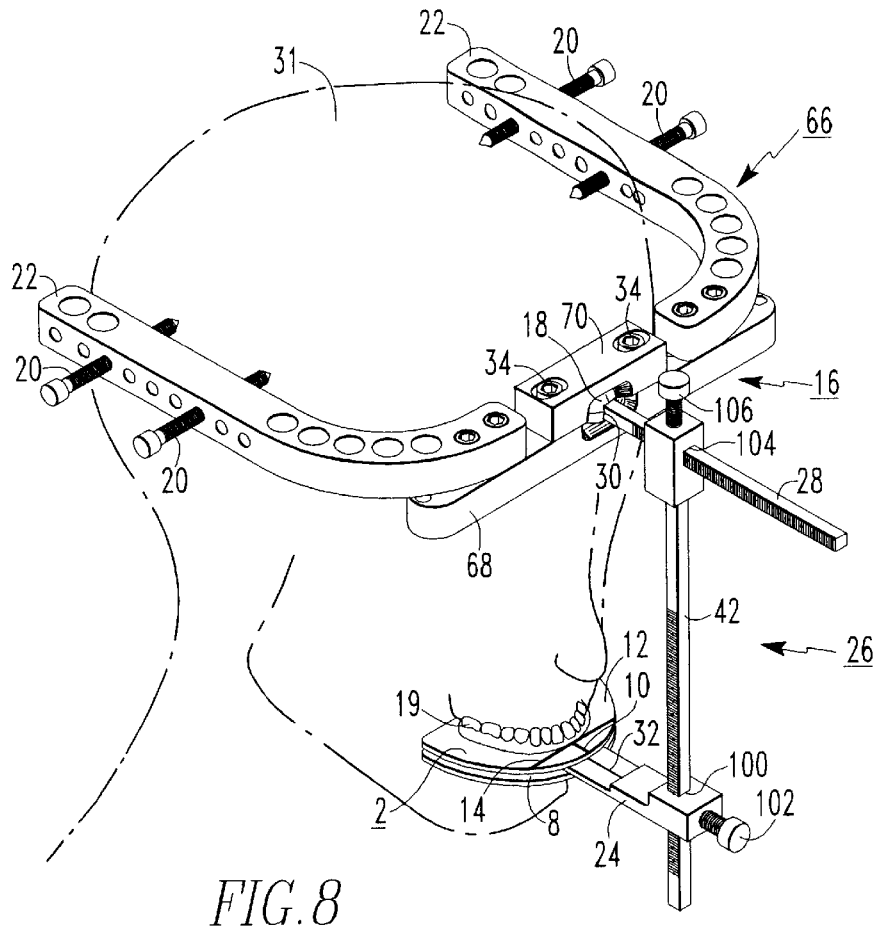
FIG. 8 is an isometric view showing the recording of reference planes on a patient's head at surgery.

As seen in FIG. 8, a base member 16 housing a swivel member 18 is secured to the patient's head by tightening screws 20 of a support structure 22 to the sides of the patient's head at surgery 31 in a vice-like manner. While holding the teeth indexing member 2 against the patient's teeth 19, a reference member 24 of a coupling member 26 is inserted into the horizontal slot 8 of the teeth indexing member 2 and a rectangular horizontal rod 28 of the coupling member 26 is inserted into a rectangular port 30 of the swivel member 18. A sagittal midline scribe 32 on the reference member 24 is aligned to the saggital scribe line 10 on the top surface 12 of the teeth indexing member 2. As seen in FIGS. 8 and 9, the rectangular port 30 of the swivel member 18 is concurrently aligned to the reference planes 5, 7, and 9 because of a right angle relationship of the reference member 24 to a rectangular vertical rod 42 and a right angle relationship of the rectangular vertical rod 42 to the rectangular horizontal rod 28. The swivel member 18 is secured in place in a vice-like manner by tightening screws 34 of the base member 16. The coupling member 26 and the teeth indexing member 2 are then removed. The port 30 of the swivel member 18 recorded the reference planes 5, 7, and 9, as seen in FIG. 9.

Figure 10:
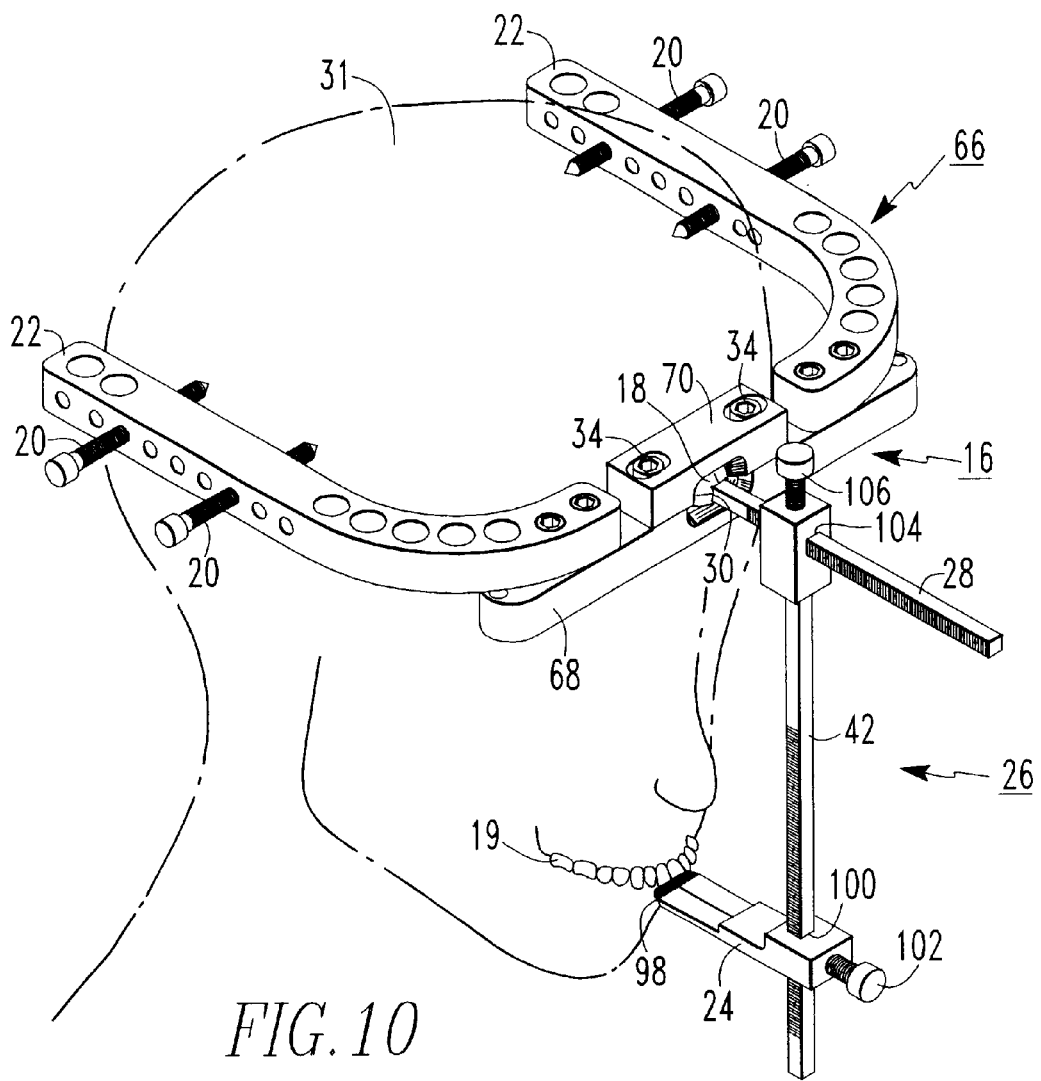
FIG. 10 is an isometric view showing a reference member indicating an original position of teeth and jaws of a patient's head.

As seen in FIG. 10, the coupling member 26 is then used to measure the original position of the teeth and jaws by inserting the horizontal rod 28 into the port 30 of the swivel member 18. The beveled end 98 of the reference member 24 is positioned at a defined point on the teeth and jaws. Measurements of the original position of the teeth and jaws are then made in the x-dimension 13 on the calibrated horizontal rod 28, in the y-dimension 15 on the calibrated vertical rod 42 and in the z-dimension 17 on the calibrated reference member 24 (x-dimension 13, y-dimension 15, and z-dimension 17 are shown in FIG. 1). The coupling member 26 is then removed.

Figure 11:
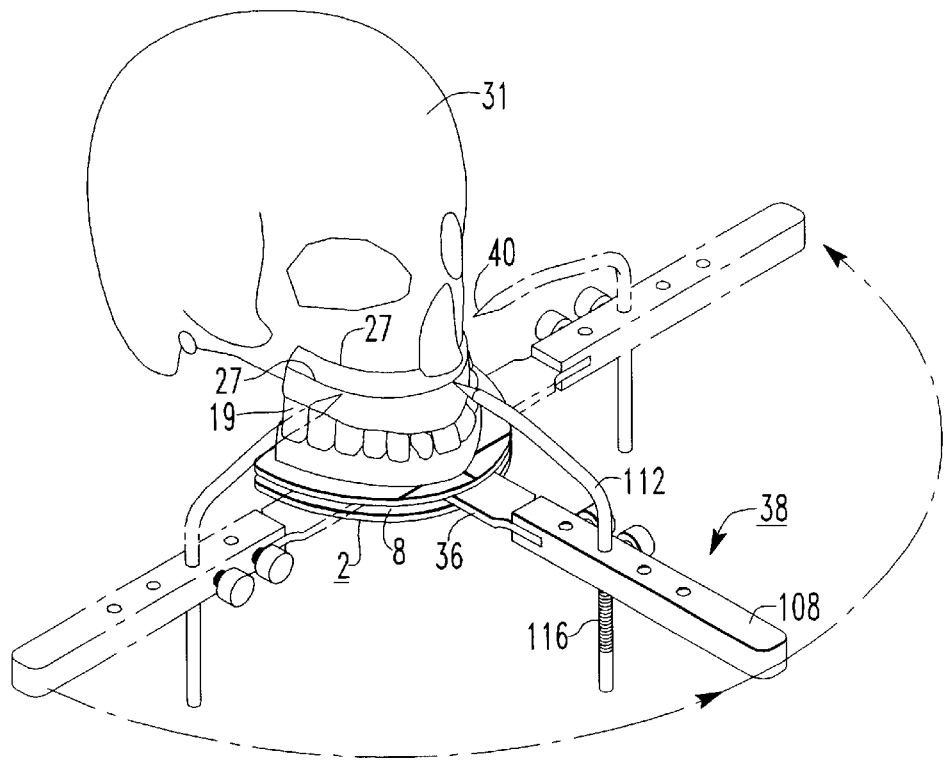
FIG. 11 is an isometric view of a patient's head at surgery with an indicator member indicating osteotomies on a jaw.

The surgeon can place the teeth indexing member 2 against the patient's teeth 19 again when the jawbone has been exposed. As seen in FIG. 11, a coupling blade 36 of an indicator member 38 is inserted into the horizontal slot 8 of the teeth indexing member 2. The calibrated pointer 112 of the indicator member 38 is used to design and measure osteotomies 27. The indicator member 38 can measure perpendicular to the horizontal reference plane 5 in the y-dimension 15. By sliding the coupling blade 36 through the horizontal slot 8 of the teeth indexing member 2, the tip 40 of the pointer 112 is moved around both sides of the jaw adapting to the contour of the bone. Osteotomy lines 27 are marked parallel to the horizontal reference plane 5.

Osteotomy lines 27 can be marked at various angles to the reference planes by using additional teeth indexing members 2 that are indexed to the teeth 19 of the dental model 21 at various angles to the reference planes.

Once the surgeon has completed the osteotomies, the teeth and jaws are mobilized and repositioned. Actual changes are made to the original position of the teeth and jaws.

Figure 14:
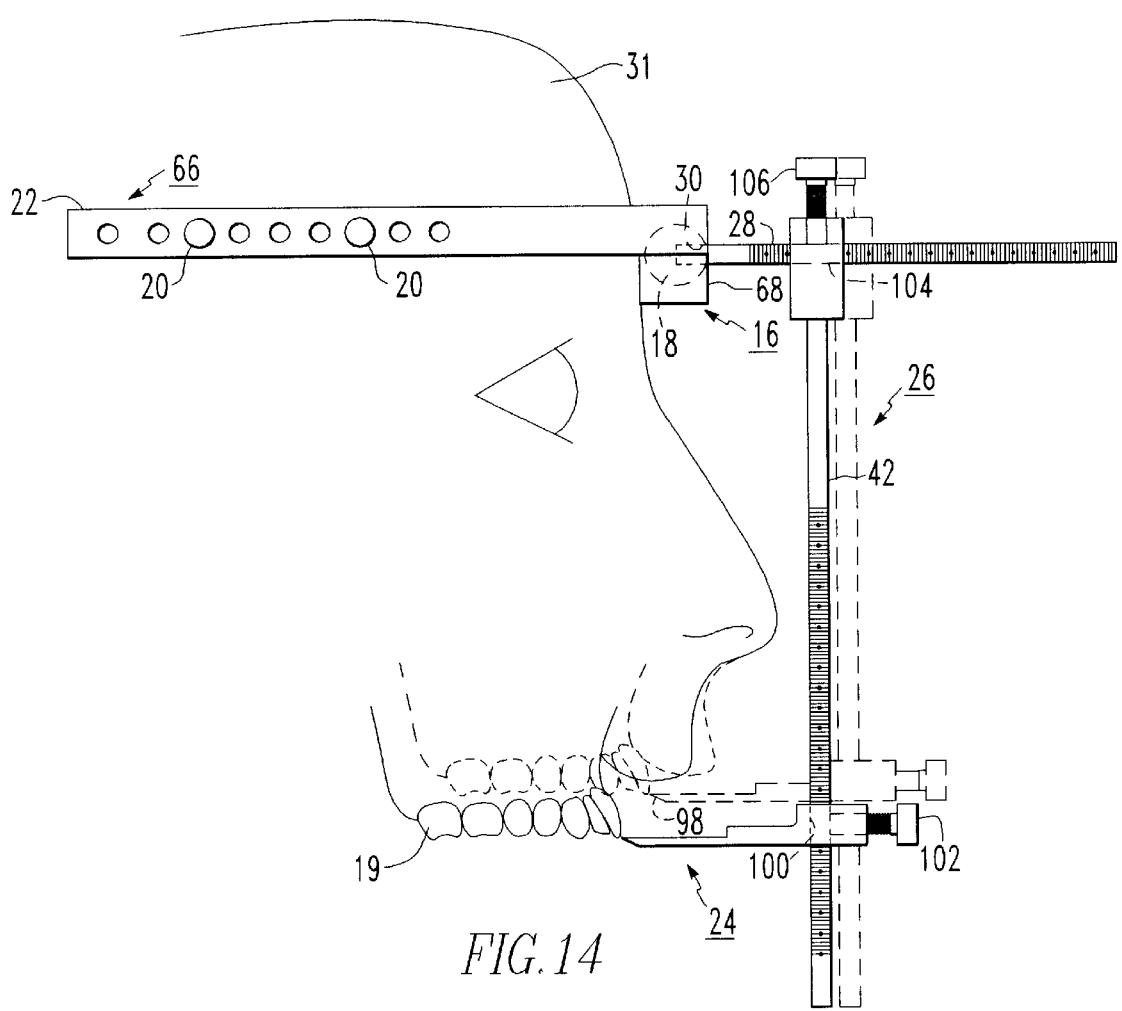
FIG. 14 is a side plan view of a patient's head depicting an actual change to an original position of the patient's upper teeth and jaw, and a depiction of a reference member and coupling member indicating a desired change to the original position of the patient's upper teeth and jaw in x- and y-dimensions.
Figure 15:
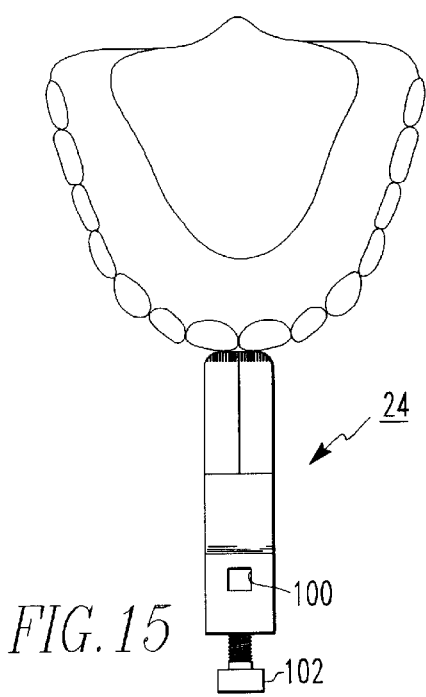
FIG. 15 is a top plan view of a patient's upper teeth and jaw and a reference member indicating an original position of the patient's upper teeth and jaw in a z-dimension.
Figure 16:
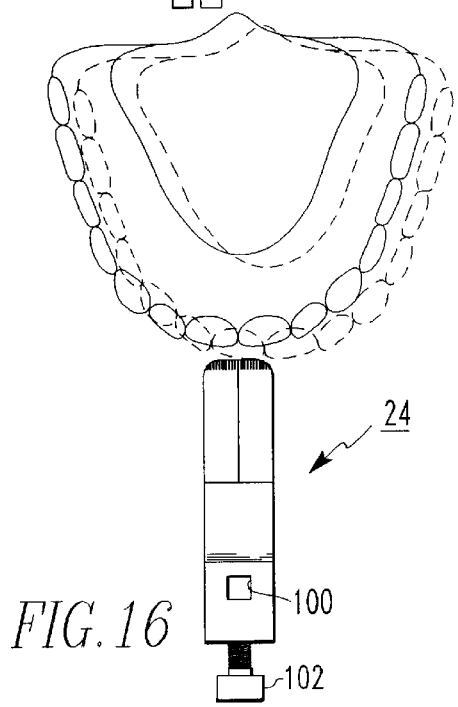
FIG. 16 is a top plan view of a patient's upper teeth and jaw depicting an actual change to an original position of the teeth and jaw and a reference member indicating a desired change to the patient's upper teeth and jaw in a z-dimension.
Figure 17:
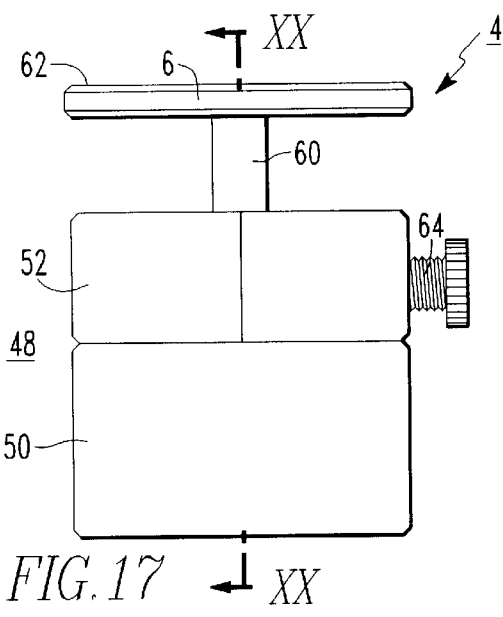
FIG. 17 is a side elevation view of an elevator.
Figure 18:
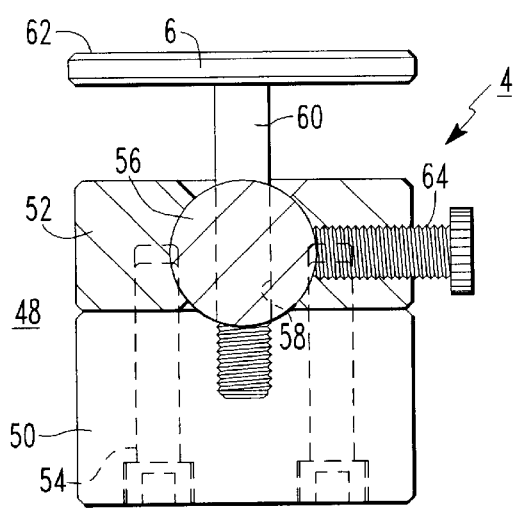
FIG. 18 is a sectional view of an elevator taken along the lines XX—XX of FIG. 17.
Figure 19:
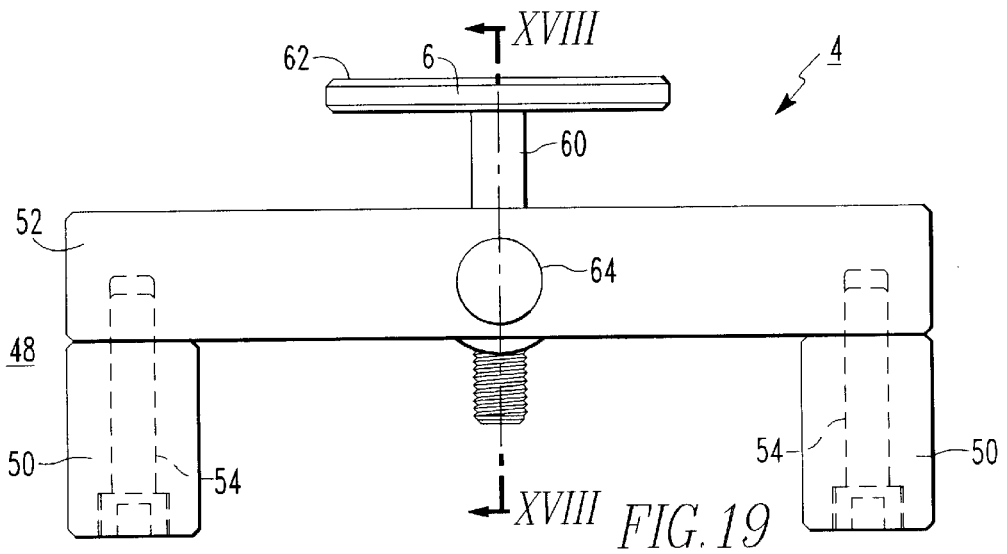
FIG. 19 is an end elevation view of an elevator.
Figure 20:
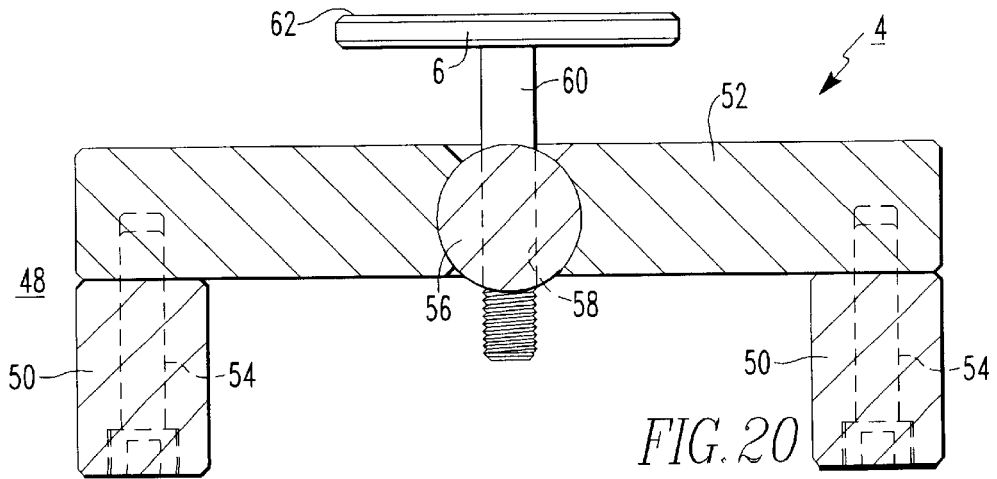
FIG. 20 is a sectional view of an elevator taken along the lines XVIII—XVIII of FIG. 19.
Figure 21:
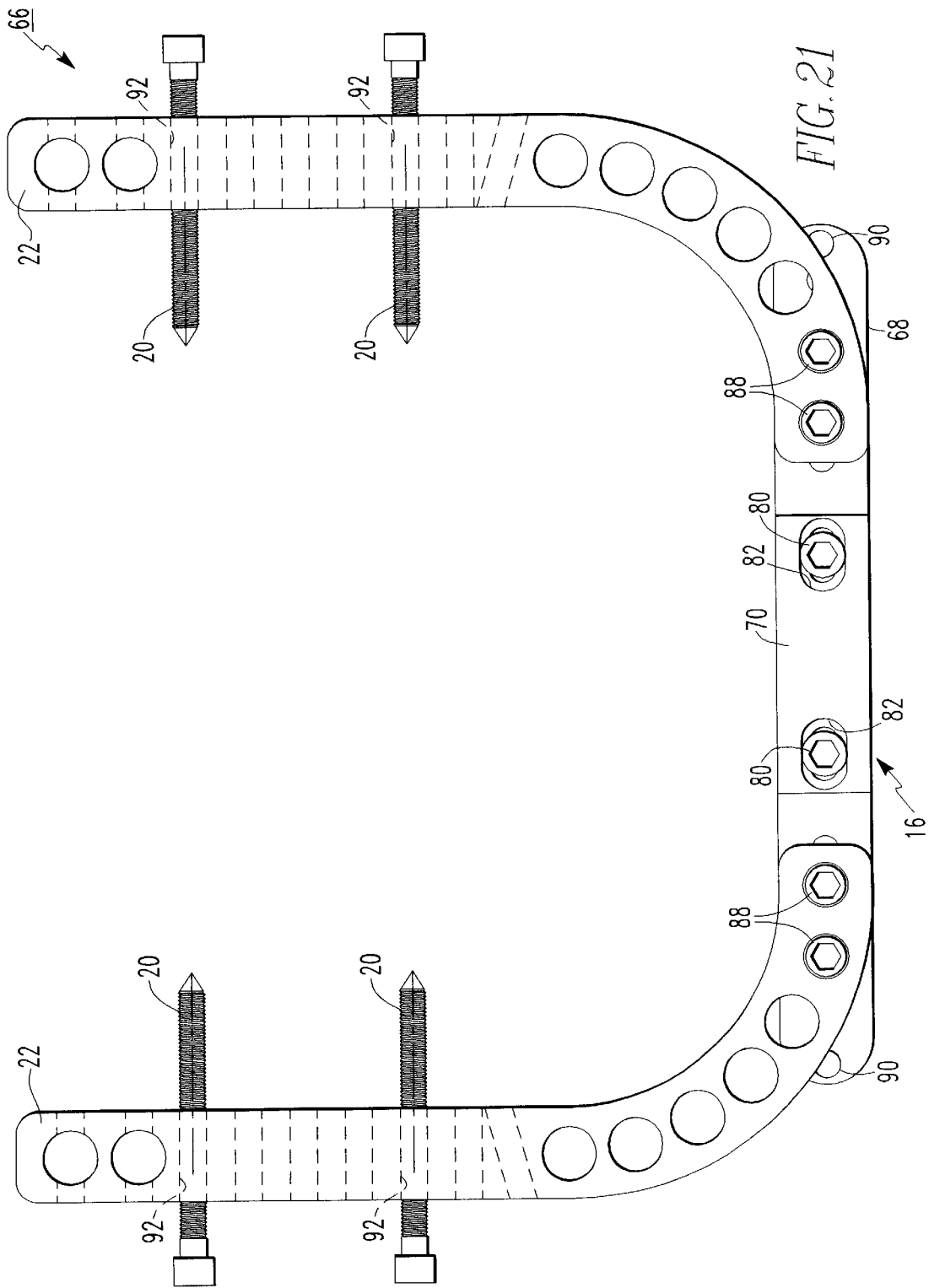
FIG. 21 is a top plan view of a cranial structure.
Figure 22:
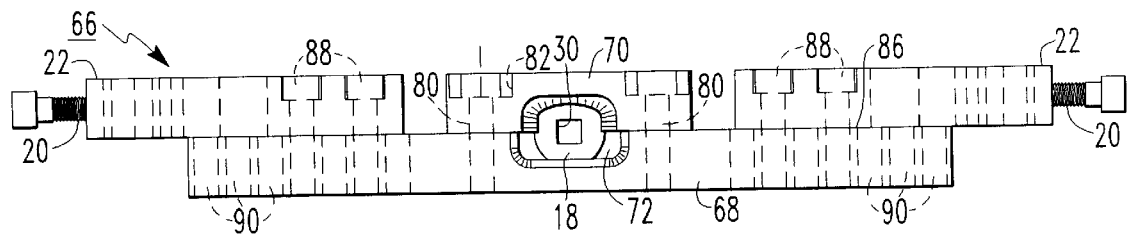
FIG. 22 is an end elevation view of a cranial structure including a swivel member and base member.
Figure 23:
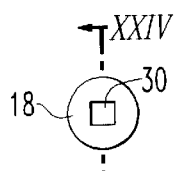
FIG. 23 is an end elevation view of a port in a swivel member.
Figure 24:
FIG. 24 is a sectional view of a swivel member taken along the lines XXIV—XXIV of FIG. 23.
Figure 25:
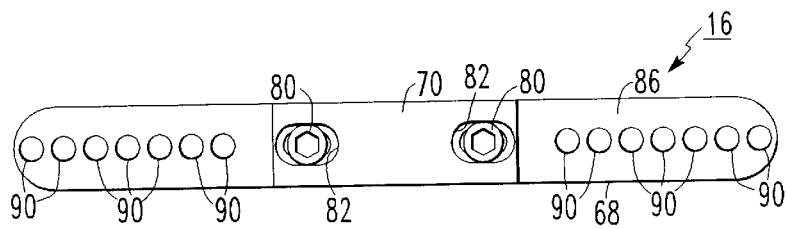
FIG. 25 is a top plan view of a base member.
Figure 26:
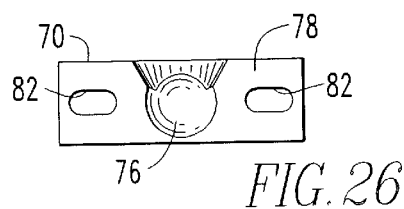
FIG. 26 is a bottom plan view of an upper block of a base member.
Figure 27:
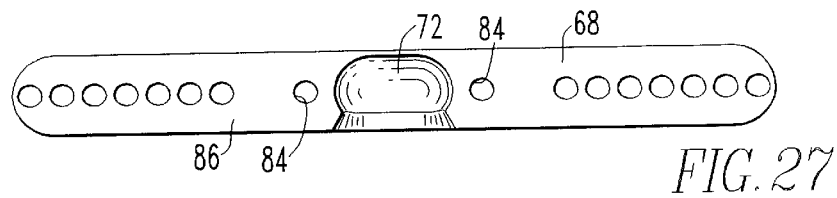
FIG. 27 is a top plan view of a lower bar of a base member.

To compare the actual changes of the teeth and jaws to the desired changes of the teeth and jaws the reference member 24 of the coupling member 26 is moved via the horizontal rod 28 and vertical rod 42 to reflect the desired presurgical changes in the x-, y-, and z-dimensions 13, 15, and 17. As seen in FIGS. 14–16, by inserting the horizontal rod 28 of the coupling member 26 into the port 30 of the swivel member 18 periodically while the teeth and jaws are being repositioned, the beveled edge 98 of the reference member 24 provides a target for relocating the defined point on the teeth and jaws to the desired position in the x-, y-, and z-dimensions 13, 15, and 17.

As seen in FIGS. 4–6, the teeth indexing member 2 is round in shape and has a flat top plate 44 and bottom plate 46 that are parallel. A horizontal slot 8 is interfaced between and parallel to the plates 44, 46. A sagittal scribe line 10 is on the top surface 12. A frontal scribe line 14 is on the top surface 12 perpendicular to the sagittal scribe line 10.

As seen in FIGS. 17–20, the elevator 4 consists of a base member 48 that is bridge-like in form. The vertical sections 50 are of the same height and parallel to each other. The horizontal section 52 is secured to the top of the vertical sections 50 by screws 54. The horizontal section 52 is flat and perpendicular to the vertical sections 50. Centered in the horizontal section 52 is a pivot ball 56 with a threaded hole 58 to receive a threaded rod 60 supporting the elevator platform 6. The top surface 62 of the elevator platform 6 is parallel to the flat surface that the elevator 4 rests on and is therefore parallel to the horizontal reference plane 5. The elevator platform 6 is raised and lowered in a parallel manner to the horizontal reference plane 5 by turning the threaded rod 60. The pivot ball 56 permits orienting the platform 6 at various angles to the reference planes by a tilting action. It is secured in place by a setscrew 64.

As seen in FIGS. 21–27, the cranial structure 66 consists of a swivel member 18, a base member 16, and two support structures 22. The base member 16 is made up of a lower rectangular bar 68 and an upper rectangular block 70. The lower bar 68 has a trough 72 on its top surface 86 along which the swivel member 18 can slide. The upper block 70 has a spherical depression 76 on its bottom surface 78 where the swivel member 18 rests. The base member 16 functions in a vice-like manner to secure the swivel member 18 by tightening the screws 80 through two elongated slots 82 in the upper block 70 into threaded holes 84 in the lower bar 68. The elongated slots 82 in the upper block 70 allow the upper block 70 to slide and permit precise centering of the swivel member 18 to the sagittal plane 7 of the patient's head. Two elongated support structures 22 are attached to the top surface 86 and to either end of the lower bar 68 by screws 88 passing through the support structures 22 into threaded holes 90 in the lower bar 68. There are multiple holes 90 in the lower bar 68 which allow the support structures 22 to be attached various distances apart in order to accommodate various head widths. The support structures 22 have multiple threaded holes 92 through their sides to accept screws 20 used to secure the cranial structure 66 to the patient's head at surgery 31.

Figure 28:
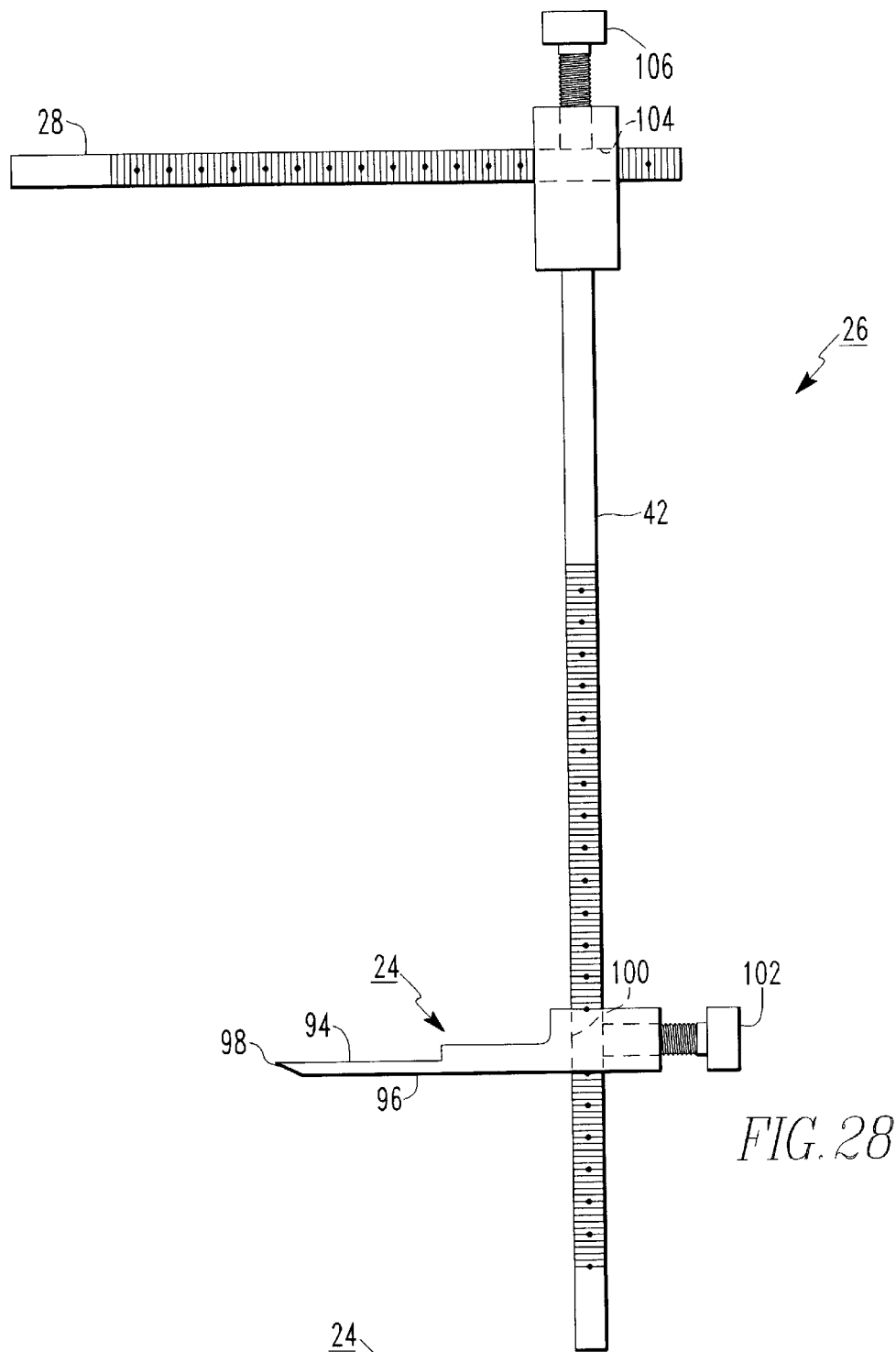
FIG. 28 is a side elevation view of a coupling member with a reference member.
Figure 29:
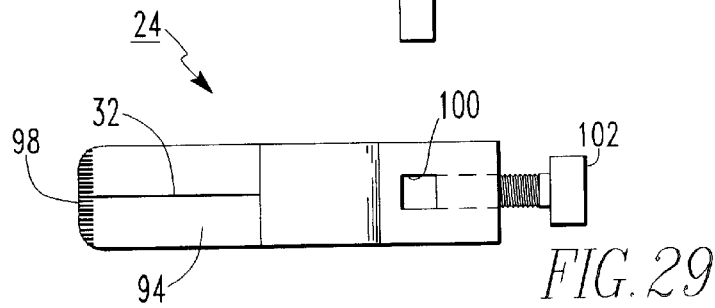
FIG. 29 is a top plan view of a reference member.

As seen in FIGS. 28 and 29, the coupling member 26 consists of a reference member 24 that is blade-like and stepped in shape. The reference member 24 has parallel flat top 94 and bottom surfaces 96. The top surface 94 has a saggital midline scribe line 32 parallel to the length of the reference member 24. When inserted into the slot 8 of the teeth indexing member 2 the reference member 24 can parallel the horizontal reference plane 5. The end 98 of the reference member 24 is perpendicular to the length of the reference member 24 and is beveled to an edge towards the top surface 94. The reference member 24 can slide along the slot 8 of the teeth indexing member 2. The top surface 94 is calibrated at the beveled end 98. The calibrated beveled end 98 when oriented parallel to the frontal plane 9 can measure in the z-dimension 17. The reference member 24 has a rectangular hole 100 through which it is slidably mounted perpendicular to the rectangular vertical rod 42. A setscrew 102 drilled through the end of the reference member 24 can secure the reference member 24 in position on the vertical rod 42. The calibrated vertical rod 42 when oriented perpendicular to the horizontal reference plane 5 can measure in the y-dimension 15. The rectangular vertical rod 42 is slidably mounted perpendicular to the horizontal rod 28 through a rectangular hole 104 at the end of the vertical rod 42. The rectangular horizontal rod 28 parallels the saggital midline scribe line 32 on the reference member 24. The rectangular horizontal rod 28 fits into the rectangular port 30 of the swivel member 18. The calibrated horizontal rod 28 when oriented parallel to the sagittal reference plane can measure in the x-dimension 13. As seen in FIGS. 8–10, the horizontal rod 28, the vertical rod 42 and the beveled end 98 of the reference member 24 provide respectively x-, y-, and z-dimensions 13, 15, and 17 for measuring relative to the reference planes of the patient's head.

Figure 12:
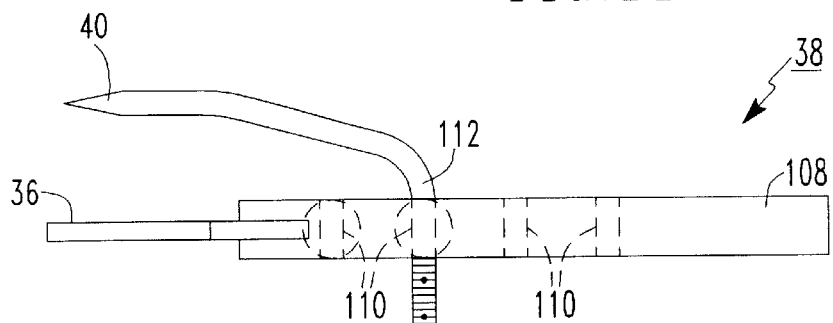
FIG. 12 is a side plan view of an indicator member.
Figure 13:
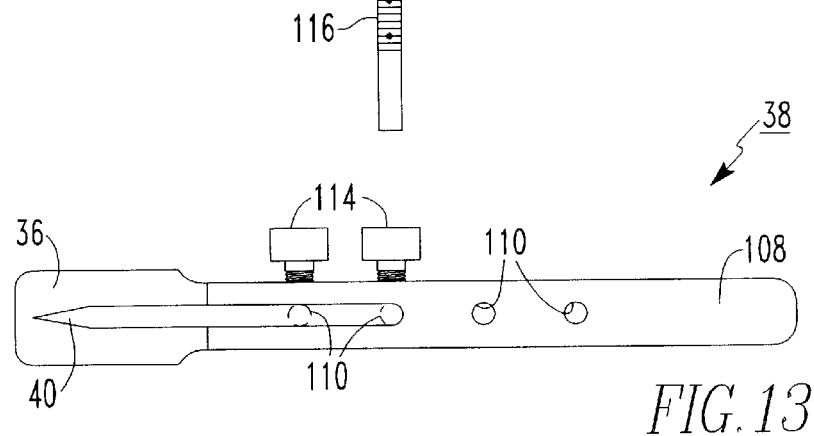
FIG. 13 is a top plan view of an indicator member.

As seen in FIGS. 12 and 13, the indicator member 38 consists of a rectangular handle 108 with a coupling blade 36 extending from one end. A pointer 112, generally L-shaped, is slidably mounted through any of the holes 110 in the handle 108. The calibrated vertical section 116 of the pointer 112 is perpendicular to the coupling blade 36 and can be secured at various heights by a setscrew 114. The holes 110 are located in the handle 108 to position the pointer 112 relative to the end of the coupling blade 36. The tip 40 of the pointer 112 is directed away in a nonparallel manner from the perpendicular section 116 of the pointer 112. The surgeon can slide the coupling blade 36 around the slot 8 of the teeth indexing member 2 to design and measure osteotomy lines 27 on the jawbone.

Various changes could be made in the above construction and method without departing from the scope of the invention as defined in the claims below. It is intended that all matter contained in the above description as shown in the accompanying drawings shall be interpreted as illustrative and not as a limitation.

I claim:

1. A method to assist in accurate placement of teeth and jaws of a patient during orthognathic surgery comprising:
   (a) establishing a reference plane for the patient's head;
   (b) deciding measurements of desired changes to be made at surgery to an original position of the teeth and jaws relative to the reference plane; and
   (c) comparing actual changes to the original position of the patient's teeth and jaws performed during orthognathic surgery relative to the reference plane with the desired changes to the original position of the teeth and jaws relative to the reference plane.

2. The method as recited in claim 1 wherein the comparison of the actual changes during orthognathic surgery with the desired changes comprises:

(a) recording the reference plane on a teeth indexing member;
(b) orienting a swivel member to the reference plane with the teeth indexing member which is coupled to the swivel member before actual changes to the original position of the patient's teeth and jaws;
(c) coupling the oriented swivel member to a reference member which indicates the original position of the teeth and jaws in a y-dimension before the original position of the teeth and jaws are changed;
(d) measuring the original position of the teeth and jaws in the y-dimension on a coupling member which couples the swivel member to the reference member before the original position of the teeth and jaws are changed by surgery;
(e) adjusting the reference member to indicate the desired changes in the y-dimension to the original position of the teeth and jaws in the y-dimension;
(f) changing the original position of the teeth and jaws by surgery;
(g) comparing the actual changes to the original position of the teeth and jaws in the y-dimension with the desired changes to the original position of the teeth and jaws in the y-dimension.

3. The method as recited in claim 1 wherein the comparison of the actual changes during orthognathic surgery with the desired changes comprises:
(a) recording the reference plane on a teeth indexing member;
(b) orienting a swivel member to the reference plane with the teeth indexing member which is coupled to the swivel member before actual changes to the original position of the patient's teeth and jaws;
(c) coupling the oriented swivel member to a reference member which indicates the original position of the teeth and jaws in an x-dimension before the original position of the teeth and jaws are changed;
(d) measuring the original position of the teeth and jaws in the x-dimension on a coupling member which couples the swivel member to the reference member before the original position of the teeth and jaws are changed by surgery;
(e) adjusting the reference member to indicate the desired changes in the x-dimension to the original position of the teeth and jaws in the x-dimension;
(f) changing the original position of the teeth and jaws by surgery;
(g) comparing the actual changes to the original position of the teeth and jaws in the x-dimension with the desired changes to the original position of the teeth and jaws in the x-dimension.

4. The method as recited in claim 1 wherein the comparison of the actual changes during orthognathic surgery with the desired changes comprises:
(a) recording the reference plane on a teeth indexing member;
(b) orienting a swivel member to the reference plane with the teeth indexing member which is coupled to the swivel member before actual changes to the original position of the patient's teeth and jaws;
(c) coupling the oriented swivel member to a reference member which indicates the original position of the teeth and jaws in a z-dimension before the original position of the teeth and jaws are changed;
(d) measuring the original position of the teeth and jaws in the z-dimension on a coupling member which couples the swivel member to the reference member before the original position of the teeth and jaws are changed by surgery;
(e) adjusting the reference member to indicate the desired changes in the z-dimension to the original position of the teeth and jaws in the z-dimension;
(f) changing the original position of the teeth and jaws by surgery;
(g) comparing the actual changes to the original position of the teeth and jaws in the z-dimension with the desired changes to the original position of the teeth and jaws in the z-dimension.

5. The method as recited in claim 1 including attaching to the patient's head a recording of the reference plane, whereby the reference plane can be reproduced relative to the patients head.

6. The method as recited in claim 1 wherein the reference plane is established in a presurgical work-up.

7. A method as recited in claim 1 including:
(a) transferring a recording of the reference plane for the patient's head to a model to perform model surgery; and
(b) transferring the recording of the reference plane from the model to the patient's head for surgery.

8. A method to assist in accurate placement of teeth and jaws of a patient during orthognathic surgery comprising:
(a) establishing reference planes for the patient's head;
(b) deciding measurements of desired changes to be made at surgery to an original position of the teeth and jaws relative to the reference planes; and
(c) comparing actual changes to the original position of the patient's teeth and jaws performed during orthognathic surgery relative to the reference planes with the desired changes to the original position of teeth and jaws relative to the reference planes.

9. The method as recited in claim 8 wherein the comparison of the actual changes during orthognathic surgery with the desired changes comprises:
(a) recording the reference planes on a teeth indexing member;
(b) orienting a swivel member to the reference planes with the teeth indexing member which is coupled to the swivel member before actual changes to the original position of the patient's teeth and jaws;
(c) coupling the oriented swivel member to a reference member which indicates the original position of the teeth and jaws in x- and y-dimensions before the original position of the teeth and jaws are changed;
(d) measuring the original position of the teeth and jaws in the x- and y-dimensions on a coupling member which couples the swivel member to the reference member before the original position of the teeth and jaws are changed by surgery;
(e) adjusting the reference member to indicate the desired changes in the x- and y-dimensions to the original position of the teeth and jaws in the x- and y-dimensions;
(f) changing the original position of the teeth and jaws by surgery;
(g) comparing the actual changes to the original position of the teeth and jaws in the x- and y-dimensions with the desired changes to the original position of the teeth and jaws in the x- and y-dimensions.

10. The method as recited in claim 8 wherein the comparison of the actual changes during orthognathic surgery with the desired changes comprises:
(a) recording the reference planes on a teeth indexing member;
(b) orienting a swivel member to the reference planes with the teeth indexing member which is coupled to the swivel member before actual changes to the original position of the patient's teeth and jaws;
(c) coupling the oriented swivel member to a reference member which indicates the original position of the teeth and jaws in y- and z-dimensions before the original position of the teeth and jaws are changed;
(d) measuring the original position of the teeth and jaws in the y- and z-dimensions on a coupling member which couples the swivel member to the reference member before the original position of the teeth and jaws are changed by surgery;
(e) adjusting the reference member to indicate the desired changes in the y- and z-dimensions to the original position of the teeth and jaws in the y- and z-dimensions;
(f) changing the original position of the teeth and jaws by surgery;
(g) comparing the actual changes to the original position of the teeth and jaws in the y- and z-dimensions with the desired changes to the original position of the teeth and jaws in the y- and z-dimensions.

11. The method as recited in claim 8 wherein the comparison of the actual changes during orthognathic surgery with the desired changes comprises:
(a) recording the reference planes on a teeth indexing member;
(b) orienting a swivel member to the reference planes with the teeth indexing member which is coupled to the swivel member before actual changes to the original position of the patient's teeth and jaws;
(c) coupling the oriented swivel member to a reference member which indicates the original position of the teeth and jaws in x- and z-dimensions before the original position of the teeth and jaws are changed;
(d) measuring the original position of the teeth and jaws in the x- and z-dimensions on a coupling member which couples the swivel member to the reference member before the original position of the teeth and jaws are changed by surgery;
(e) adjusting the reference member to indicate the desired changes in the x- and z-dimensions to the original position of the teeth and jaws in the x- and z-dimensions;
(f) changing the original position of the teeth and jaws by surgery;
(g) comparing the actual changes to the original position of the teeth and jaws in the x- and z-dimensions with the desired changes to the original position of the teeth and jaws in the x- and z-dimensions.

12. The method as recited in claim 8 wherein the comparison of the actual changes during orthognathic surgery with the desired changes comprises:
(a) recording the reference planes on a teeth indexing member;
(b) orienting a swivel member to the reference planes with the teeth indexing member which is coupled to the swivel member before actual changes to the original position of the patient's teeth and jaws;
(c) coupling the oriented swivel member to a reference member which indicates the original position of the teeth and jaws in x-, y-, and z-dimensions before the original position of the teeth and jaws are changed;
(d) measuring the original position of the teeth and jaws in the x-, y-, and z-dimensions on a coupling member which couples the swivel member to the reference member before the original position of the teeth and jaws are changed by surgery;
(e) adjusting the reference member to indicate the desired changes in the x-, y-, and z-dimensions to the original position of the teeth and jaws in the x-, y-, and z-dimensions;
(f) changing the original position of the teeth and jaws by surgery;
(g) comparing the actual changes to the original position of the teeth and jaws in the x-, y-, and z-dimensions with the desired changes to the original position of the teeth and jaws in the x-, y-, and z-dimensions.

13. A method as recited in claim 8 including:
(a) transferring a recording of the reference planes for the patient's head to a model to perform model surgery; and
(b) transferring the recording of the reference planes from the model to the patient's head for surgery.

14. An apparatus to assist in accurate placement of teeth and jaws of a patient during orthognathic surgery comprising:
(a) a movable ball supported in a base member, the ball having a port to receive a horizontal rod;
(b) a support structure joined to the base member for securing the base member to a human head;
(c) a horizontal rod inserted into the ball;
(d) a vertical rod slidably supported by the horizontal rod, the vertical rod perpendicular to the horizontal rod; and
(e) a reference member slidably mounted on the vertical rod and perpendicular to the vertical rod.

15. An apparatus as recited in claim 14 wherein the reference member, the vertical rod, and the horizontal rod have calibrations.

16. An apparatus as recited in claim 14 including a teeth indexing member coupled to the reference member.

17. An apparatus as recited in claim 16 wherein the teeth indexing member comprises:
(a) a plate with a horizontal slot having a top surface; and
(b) a tooth indexable top surface.

18. An apparatus to assist in accurate placement of teeth and jaws of a patient during orthognathic surgery comprising:
(a) a teeth indexing member; and
(b) an indicator member having a pointer, the pointer extends from the indicator member, the indicator member is coupled to the teeth indexing member so that when the teeth indexing member is in position on the patient's teeth the pointer can touch the patient's jaw, whereby the pointer can design an osteotomy on the jaw of the patient.

19. An apparatus as recited in claim 18 wherein the teeth indexing member comprises:
(a) a plate with a horizontal slot having a top surface; and
(b) a tooth indexable top surface.

20. An apparatus as recited in claim 19 in which the indicator member comprises:
(a) a handle having a coupling blade that is slidably engaged with the slot of the teeth indexing member; and (b) wherein the pointer is slidably supported in a perpendicular manner by the handle and the pointer has a tip directed away in a nonparallel manner from the perpendicular section of the pointer and toward the coupling blade.

21. A method to assist in accurate placement of teeth and jaws of a patient during orthognathic surgery comprising:
    (a) deciding a design for an osteotomy relative to a reference plane;
    (b) recording the reference plane on a teeth indexing member;
    (c) positioning the teeth indexing member on a patient's teeth; and
    (d) indicating a design for an osteotomy on a patient's jaw relative to the reference plane.

22. A method to assist in accurate placement of teeth and jaws of a patient during orthognathic surgery comprising:
    (a) recording a reference plane used with presurgical records; and
    (b) transferring the recording of the reference plane used with presurgical records to the patient's head at surgery.

* * * * *